United States Patent [19]

Johnson et al.

[11] 4,411,893
[45] Oct. 25, 1983

[54] TOPICAL MEDICAMENT PREPARATIONS

[75] Inventors: Dee L. Johnson, Woodbury; Therese A. Senta, Minneapolis; Larry M. Sirvio, Cottage Grove, all of Minn.

[73] Assignee: Minnesota Mining and Manufacturing Company, St. Paul, Minn.

[21] Appl. No.: 422,891

[22] Filed: Sep. 24, 1982

Related U.S. Application Data

[63] Continuation-in-part of Ser. No. 292,809, Aug. 14, 1981, abandoned, which is a continuation of Ser. No. 187,089, Sep. 15, 1980, abandoned.

[51] Int. Cl.$^3$ ...................... A61K 31/71; A61K 31/13
[52] U.S. Cl. .................................. 424/181; 424/227; 424/240; 424/243; 424/248.4; 424/248.54; 424/248.57; 424/251; 424/267; 424/274; 424/325; 424/330

[58] Field of Search ............... 424/181, 227, 240, 243, 424/248.4, 248.54, 248.57, 251, 267, 274, 325, 330

[56]     References Cited
            PUBLICATIONS

Armour–Chem. Abst., vol. 72, (1970), p. 6190v.

*Primary Examiner*—Sam Rosen
*Attorney, Agent, or Firm*—Donald M. Sell; James A. Smith; Carolyn A. Bates

[57]             ABSTRACT

Topical therapeutic compositions are disclosed which contain from about 0.1 to 70 percent by weight of a water-soluble tertiary amine oxide and a therapeutic agent selected from the group consisting of erythromycin, benzoyl peroxide, hydrocortisone, tetracycline, 5-fluorouracil, and propranolol. The amine oxide enhances penetration of the therapeutic agent into and through the skin.

8 Claims, No Drawings

TOPICAL MEDICAMENT PREPARATIONS

This application is a continuation-in-part of Ser. No. 292,809, filed Aug. 14, 1981 which was a continuation of Ser. No. 187,089 filed Sept. 15, 1980, both now abandoned.

This invention relates to an improved method and compositions for the topical treatment of animal (including human) tissues. More particularly, the invention relates to penetration aids which, when incorporated into topical therapeutic compositions, enhance the penetration of various therapeutic agents into and/or through the skin of animals.

The skin is designed by nature to provide an effective barrier against the penetration of foreign substances into the body. Although generally beneficial, the barrier properties of the skin often interfere with the effective delivery of topically-applied medicaments to their intended site of action. To overcome this problem, a number of chemical penetration aids have been developed. For example, U.S. Pat. No. 3,326,768 discloses that the presence of a phosphine oxide surfactant in antiperspirant compositions containing anticholinergic compounds provides more efficient absorption of the active compounds at the site of application. U.S. Pat. No. 3,472,931 discloses that percutaneous absorption of certain therapeutic agents is enhanced by incorporating the agent into a vehicle containing a lower alkyl amide. Compositions for enhancing the penetration of pharmacologically active agents through the skin comprising a sugar ester in combination with a sulfoxide or phosphine oxide are disclosed in U.S. Pat. No. 3,896,238.

Dimethylsulfoxide (DMSO) is regarded as one of the most effective penetration enhancers discovered to date. However, it has been shown that DMSO has some undesirable side effects that preclude wide spread applications for human (as well as most animal) uses. Accordingly, prior to the present invention there existed a need for a penetration aid for topical therapeutic compositions which would be effective for a broad spectrum of therapeutic agents and cause a minimum of undesirable side effects.

According to the present invention, it has been discovered that certain water-soluble amine oxide compounds are extremely effective in enhancing penetration of certain therapeutic agents into and through the skin with minimal toxic side effects. Amine oxides have been used heretofore in compositions which contact the skin, most notably as solubilizers or emulsifying agents in certain cosmetic formulations and shampoos. U.K. Pat. Application No. GB2,004,185A discloses cosmetic preparations such as facial lotions and shampoos containing certain alkyl amine oxides as solubilizing agents. U.S. Pat. No. 4,048,338 discloses cosmetic compositions containing certain novel morpholine oxides. The compounds are described as having many desirable attributes of particular value in emulsification, cleansing and detergency. They are further described as having a non-irritating and even anti-irritating effect on the skin. Other amine oxides suggested for use in hair-treating compositions are disclosed in U.S. Pat. Nos. 3,098,794, 3,499,930 and 4,166,845. However, prior to the present invention, it was unappreciated that water-soluble amine oxides could be used to enhance penetration of therapeutic agents into and/or through the skin.

According to the present invention there are provided compositions for application to animal skin comprising: (1) an effective amount of a therapeutic agent selected from the group consisting of erythromycin, benzoyl peroxide, hydrocortisone, tetracycline, 5-fluorouracil and propranolol; (2) about 0.1 to 70 percent by weight of at least one water-soluble amine oxide; and (3) at least 1 molecule of water for every molecule of amine oxide. Other ingredients conventionally used in topical preparations such as water-soluble alcohols, glycols, surfactants, perfumes, preservatives, hydrophilic polymers, emulsifiers, natural and synthetic oils, lanolin, fatty alcohols, etc. may be added to the compositions. Hydrophilic polymers may be added to increase the viscosity or gel the composition and include such materials as hydrophilic acrylic polymers, polyvinyl alcohol, gelatin, hydroxyethyl cellulose, carboxymethyl cellulose, gum tragacanth, gum karaya, gum arabic and other thickening agents known to those skilled in pharmaceutical formulations.

Compositions of the invention exhibit enhanced penetration of the therapeutic agent through animal skin when compared to similar compositions containing no amine oxide. The amine oxides, when used in the concentration range specified, exhibit minimal toxic side effects.

The term "water-soluble" as used to characterize the amine oxide compounds means at least one percent solubility in water, i.e., one gram of amine oxide completely dissolves in 99 grams of water. It is believed that the polarity of the nitrogen-oxygen configuration of the amine oxides is the most important feature of this invention. The hydrocarbon moiety appended thereto is important only to the extent that it does not appreciably alter the electronic configuration of the —N→O and that its (the hydrocarbon portion) segment weight remains small enough to insure that the entire molecule maintains its water solubility.

In general, amine oxide compounds useful in the practice of the present invention may be characterized as water-soluble tertiary amine oxides of the group consisting of:

Formula 1 wherein $R_1$, $R_2$ and $R_3$ are saturated or unsaturated aliphatic radicals optionally containing ether or amide linkages and/or pendent hydroxyl groups and the total number of carbon atoms in $R_1+R_2+R_3$ does not exceed 28; and

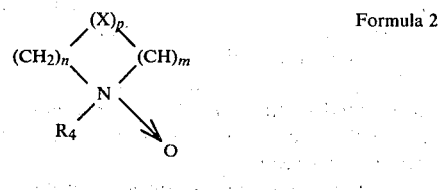

Formula 2 wherein X is —O— or

$R^4$ and $R^5$ are saturated or unsaturated aliphatic radicals each containing 1 to 18 carbon atoms optionally containing ether linkages or pendent hydroxyl groups, p is 0 or 1, n=2 or 3, and m is 2, 3 or 4.

The preferred amine oxides of Formula 1 are those wherein the number of carbon atoms in the hydrocarbon portion ($R_1+R_2+R_3$) does not exceed 18. Examples of preferred compounds of Formula 1 include:
trimethylamine oxide
tributylamine oxide
diheptylmethylamine oxide
dimethylheptylamine oxide
dimethyloctylamine oxide
dimethyldecylamine oxide
dimethyldodecylamine oxide
dimethylcocoamidopropylamine oxide
dipropyl-6-hydroxyhexylamine oxide
dicylohexylmethylamine oxide Preferred amine oxides of Formula 2 are:
N-cocomorpholine-N-oxide
N-methylpyrrolidine-N-oxide
N-methylmorpholine-N-oxide
N-methylpiperidine-N-oxide The amine oxides useful in the practice of the invention are either commercially available or readily prepared by known methods such as those described in U.S. Pat. Nos. 3,223,647 and 3,447,939 and Great Britain Pat. No. 437,566.

The amount of amine oxide incorporated into the topical preparations can range from about 0.1 to 70 percent by weight of the composition and can include mixtures of two or more amine oxides. The optimum concentration of any particular combination of amine oxide and a therapeutic agent will depend upon a number of factors such as potency of the therapeutic agent and the degree and speed of penetration, and can be readily determined empirically using the standard penetration test defined hereinbelow. In many cases, maximum penetration of the therapeutic agent does not occur at the highest concentration of amine oxide. The preferred concentration of amine oxide is generally between 2 and 10 percent by weight of the composition. The therapeutic agent will generally be present at a concentration of about 1 to 5 percent.

The compositions of the invention preferably contain from about 1 to 99 percent by weight of water. Water is the preferred common vehicle for the combination of amine oxide and therapeutic agent. In some instances, as indicated previously, a cosolvent may be added including, for example, isopropanol or propylene glycol.

The specific therapeutic agents incorporated into compositions of the invention include benzoyl peroxide used in the treatment of acne, tetracyline and erythromycin used in the treatment of microbial infections, hydrocortisone used in the treatment of inflammation, 5-fluorouracil used in the treatment of actinic keratosis and propanolol used as an antihypertensive drug.

Compositions of the invention for use on skin may be formulated in the conventional manner using pharmaceutically acceptable extending media such as gels, lotions and creams.

A typical gel composition may contain, for example, 1 percent hydroxyethyl cellulose. Typical lotion and cream vehicles are illustrated as follows.

| LOTION: Parts by Weight | Ingredient |
|---|---|
| 5 | polyoxyethylene-40-stearate |
| 3 | sorbitan monostearate |
| 12 | *mixture of lanolin, mineral oil and lanolin alcohol |
| 6 | cetyl alcohol |
| 20 | soybean oil |
| 53.7 | water |
| 0.2 | methyl paraben |
| 0.1 | propyl paraben |

*Amercol ® BL (Amerchol Corp., Edison, N.J.)

| CREAM: Parts by Weight | Ingredient |
|---|---|
| 3 | polyoxyethylene-40-stearate |
| 2.5 | sorbitan monostearate |
| 10 | soybean oil |
| 10 | *mixture of lanolin, mineral oil and lanolin alcohol |
| 1 | cetyl alcohol |
| 73.2 | water |
| 0.2 | methyl paraben |
| 0.1 | propyl paraben |

*Amerchol ® BL

Penetration Test

To evaluate the ability of amine oxides to enhance penetration of therapeutic agents into or through animal skin, a standard assay using hairless mouse skin was used. (See T. J. Franz, Journal of Investigative Dermatology 64, 190 (1975) and T. J. Franz, Current Problems in Dermatology 7, 55 (1978)). A two square centimeter piece of hairless mouse skin (2–3 month old male-HRS/J) was placed over a reservoir in contact with 10 milliliters of 0.9% saline. A 0.05 milliliter solution or suspension of the therapeutic agent and amine oxide in water was applied to the top of the mouse skin. The diffusion cell was placed in a chamber with the temperature maintained at 32° C. with 50% relative humidity. Five milliliter aliquots of saline were withdrawn (and replaced with fresh saline solution) from the reservoir at 2, 4, 8, and 24 hours after the therapeutic agent was applied and assayed for the total amount of therapeutic agent which had penetrated. The results obtained are the percent of the total amount of drug which penetrated the skin within 24 hours. These results were compared to a control solution or suspension of the drug without amine oxide. In some cases, i.e., where the drug had very low water solubility, the control vehicle was a mixture of ethanol and water. The presence of ethanol did not have a significant effect on drug penetration. In some cases, positive controls were also tested for purposes of comparisons. Each test value and control value obtained was the average of two duplicate penetration assays performed on separate halves of the same mouse skin. Compositions according to the invention showed at least 50 percent more drug penetration after 24 hours than their corresponding control.

Further understanding of the invention will be facilitated by reference to the following non-limiting examples. Where penetration data is reported as the average of two or more tests, this is intended to mean two or more tests on different mouse skins, i.e., four or more individual runs, since each skin provides enough surface area for two runs.

EXAMPLE 1

Synthesis of N-methyl pyrrolidine-N-oxide

Twenty-five ml 30% hydrogen peroxide was slowly added to 8.5 g N-methyl pyrrolidine using an ice bath to maintain the reaction temperature below 40° C. After the addition of the hydrogen peroxide was complete, the reaction was stirred overnight at room temperature. The excess hydrogen peroxide was decomposed by stirring the reaction mixture with 1 mg platinum black for 2 hours. The reaction mixture was filtered through Hyflo ® filter-aid. Most of the water was removed in vacuo, leaving 12.0 g of a light brown liquid. Analysis by NMR showed that the amine oxide solution contained 24% water (mole basis). This corresponds to 1.8 moles water per mole of N-methyl pyrrolidine-N-oxide.

EXAMPLE 2

Synthesis of N-methyl piperidine-N-oxide

Following the procedure from Example 1, 9.9 g of N-methyl piperidine was treated with 30 ml of 30% hydrogen peroxide to give 16.0 g of light yellow liquid. NMR analysis showed 3½ moles water per mole of amine oxide (34% water).

EXAMPLE 3

Synthesis of tributyl amine oxide

To a solution of 75 g of 85% m-chloroperoxybenzoic acid in 300 ml ether was added 58.2 g tributyl amine. After stirring the reaction mixture for 1 hour at room temperature, the ether was removed in vacuo. After adding 300 ml chloroform, the solution was extracted several times with 25% sodium hydroxide solution to remove m-chlorobenzoic and unreacted m-chloroperoxybenzoic acids. The chloroform was removed in vacuo to give 45 g of colorless liquid. The resulting liquid was dissolved in petroleum ether and cooled in an ice bath to give a semi-solid material which, when recrystallized from petroleum ether, gave 9.0 g of white crystalline needles (m.p. 57°-58° C.) NMR analysis showed 1 mole of water per mole of tributyl amine oxide.

EXAMPLE 4

Synthesis of Dimethyloctyl amine oxide

To 35 g of dimethyloctyl amine was added slowly 150 ml of 30% hydrogen peroxide. After stirring overnight at room temperature, the excess hydrogen peroxide was destroyed by adding 1 mg platinum black. The reaction mixture was filtered through Hyflo ® filter-aid and then extracted with ether to remove any unreacted amine. Most of the water was evaporated in vacuo leaving 40 g of a semisolid material which could not be made to crystallize. NMR analysis showed 4½ moles water per mole of amine oxide (32% water).

EXAMPLE 5

Synthesis of Dimethylheptyl amine oxide

To 28.6 g of dimethylheptyl amine was added slowly 100 ml 30% $H_2O_2$ as in Example 4 to give the dimethylheptyl amine oxide. NMR showed the resulting semisolid material to contain 29% water and 71% of the amine oxide.

EXAMPLE 6

Synthesis of Diheptylmethyl amine oxide

To a solution of 6.6 g of diheptylmethyl amine in 25 ml tetrahydrofuran (THF) was added 12 ml 30% hydrogen peroxide. The reaction mixture was refluxed for 24 hours, cooled to room temperature and then stirred with 0.2 mg platinum black overnight. After filtering the reaction mixture through Hyflo ® filter-aid, the THF was removed in vacuo. The aqueous solution was extracted with 100 ml ether. The aqueous portion of the extraction was allowed to stand for several days to allow most of the water to evaporate. The resulting solution was found to be 40% water and 60% diheptylmethyl amine oxide by NMR analysis.

EXAMPLE 7

Synthesis of Dipropyl-6-hydroxyhexyl amine oxide

To 44 g of dipropyl-6-hydroxyhexyl amine was added slowly 11.0 g of 30% hydrogen peroxide. After stirring overnight at room temperature, the reaction mixture was stirred with 0.2 platinum black for several hours followed by filtration through Hyflo ® filter-aid. After extraction with 50 ml ether, the aqueous phase was evaporated in vacuo to remove most of the water, leaving 2.0 g of dipropyl-6-hydroxyhexyl amine oxide. NMR analysis showed that there was 30% water present.

EXAMPLE 8

Synthesis of Dicyclohexylmethyl amine oxide

To a solution of 8.0 g of dicyclohexylmethylamine in 50 ml of tetrahydrofuran (THF) was added slowly 15 ml 30% hydrogen peroxide. The reaction mixture was refluxed overnight. The THF was removed in vacuo followed by stirring with 0.2 mg platinum black to destroy any remaining hydrogen peroxide. After filtering through Hyflo ® filter-aid, the aqueous solution was allowed to stand for several days to allow most of the water to evaporate leaving 7.9 grams of the corresponding amine oxide solution. NMR analysis showed that it also contained 25% water and 75% dicyclohexylmethylamine oxide.

EXAMPLE 9

Erythromycin

Using the hairless mouse skin penetration test described herein above, the results in Table I indicate that aqueous amine oxides significantly enhanced erythromycin penetration in comparison to an ethanol-water control.

TABLE I

| Percent Penetration of 1% Erythromycin Through Hairless Mouse Skin in 24 Hours | |
|---|---|
| Penetration Aid | |
| 2% Dimethyl n-alkyl ($C_{14}$ - 50%, $C_{12}$ - 40%, $C_{16}$ - 10%) Amine Oxide[1] | 73.6 |
| 5% Dimethyl n-alkyl ($C_{14}$ - 50%, $C_{12}$ - 40%, $C_{16}$ - 10%) Amine Oxide[1] | 46.2 |
| 10% Dimethyl n-alkyl ($C_{14}$ - 50%, $C_{12}$ - 40%, $C_{16}$ - 10%) Amine Oxide[1] | 15.2 |
| 2% N—cocomorpholine-N—oxide[2] | 27.0 |
| 5% N—cocomorpholine-N—oxide[2] | 32.8 |
| 10% N—cocomorpholine-N—oxide[2] | 19.0 |
| 10% Dicyclohexylmethyl amine oxide | 20.2 |
| 30% Dicyclohexylmethyl amine oxide | 16.8 |
| Control | |

TABLE I-continued
Percent Penetration of 1% Erythromycin Through Hairless Mouse Skin in 24 Hours

| | |
|---|---|
| Ethanol-water (2/1) | 7.5[3] |

[1] Barlox ® 14 from Lonza Inc., Fairlawn, New Jersey
[2] Barlox ® NCM
[3] Average of 2 determinations It was noted that there is not a linear relationship between the concentration of the amine oxide and the percent erythromycin penetrated.

EXAMPLE 10

Benzoyl peroxide

Considerable enhancement of benzoyl peroxide penetration through skin by aqueous amine oxides is illustrated in the following Table II.

TABLE II
Percent Penetration of 5% Benzoyl Peroxide Through Hairless Mouse Skin in 24 Hours

| Penetration Aid | |
|---|---|
| 2% Dimethyl Decyl Amine Oxide[1] | *12.8 |
| 5% Diemthyl Decyl Amine Oxide[1] | *14.8 |
| 10% Dimethyl Decyl Amine Oxide[1] | 17.4 |
| 2% Dimethyl n-alkyl ($C_{12}$ - 69%, $C_{14}$ - 25%, $C_{16}$ - 6%) Amine Oxide[2] | *16.8 |
| 5% Dimethyl n-alkyl ($C_{12}$ - 69%, $C_{14}$ - 25%, $C_{16}$ - 6%) Amine Oxide[2] | *22.2 |
| 2% Dimethyl n-alkyl ($C_{14}$ - 50%, $C_{12}$ - 40%, $C_{16}$ - 10%) Amine Oxide[3] | *24.2 |
| 5% Dimethyl n-alkyl ($C_{14}$ - 50%, $C_{12}$ - 40%, $C_{16}$ - 10%) Amine Oxide[3] | *22.8 |
| 2% Dimethyl Cocamidopropyl Amine Oxide[4] | *18.9 |
| 5% Dimethyl Cocoamidopropyl Amine Oxide[4] | *18.2 |
| 2% N—cocomorpholine-N—oxide[5] | *31.6 |
| 5% N—cocomorpholine-N—oxide[5] | *30.5 |
| 2% Dicyclohexyl Methyl Amine Oxide | 7.2 |
| 5% Dicyclohexyl Methyl Amine Oxide | *18.8 |
| 10% Dicyclohexyl Methyl Amine Oxide | *18.0 |
| Controls | |
| Ethanol/water (2/1) | *3.1 |
| 70% DMSO - 20% water - 5% acetone | *23.6 |
| Commercial Controls (contain an additional 1% $^{14}$C—benzoyl peroxide) | |
| Persagel ®[6] | *9.8 |
| Persadox ®[7] | *1.9 |
| Desquam-X ®[8] | *8.0 |

*Avg of 2 or more determinations
[1] Barlox ® 10S
[2] Barlox ® 12
[3] Barlox ® 14
[4] Barlox ® C
[5] Barlox ® NCM
[6] As sold, contains 5% benzoyl peroxide, acetone, carboxyvinyl polymer, triethanol amine, sodium lauryl sulfate, propylene glycol, and water (Texas Pharmacal)
[7] As sold, contains 5% benzoyl peroxide, cetyl alcohol, propylene glycol, sodium lauryl sulfate, and water (Texas Pharmacal)
[8] As sold, contains 5% benzoyl peroxide, laureth-4, carbomer 940, diisopropyl amine, disodium edetate, and water (Westwood Pharmaceuticals)

EXAMPLE 11

Hydrocortisone

TABLE III
Percent Penetration of 1% Hydrocortisone in 24 Hours

| Penetration Aid | |
|---|---|
| 5% Tributyl Amine Oxide | 10.7 |
| 10% Tributyl Amine Oxide | 12.0 |
| 20% Tributyl Amine Oxide | 12.0 |
| 2% Dicyclohexyl Methyl Amine Oxide | 13.8 |
| 5% Dicyclohexyl Methyl Amine Oxide | 17.8 |
| 10% Dicyclohexyl Methyl Amine Oxide | 19.0 |
| 10% Dimethyl Heptyl Amine Oxide | 7.7 |
| 2% Dimethyl Octyl Amine Oxide | 6.4 |
| 2% Dimethyl Decyl Amine Oxide[1] | 9.3 |
| 5% Dimethyl Decyl Amine Oxide[1] | 17.9 |
| 10% Dimethyl Decyl Amine Oxide[1] | 8.4 |
| 2% Dimethyl N—Alkyl ($C_{12}$, 69%; $C_{14}$, 25%; $C_{16}$, 6%) Amine Oxide[2] | *11.0 |
| 5% Dimethyl N—Alkyl ($C_{12}$, 69%; $C_{14}$, 25%; $C_{16}$, 6%) Amine Oxide[2] | *9.8 |
| 10% Dimethyl N—Alkyl ($C_{12}$, 69%; $C_{14}$, 25%; $C_{16}$, 6%) Amine Oxide[2] | *13.8 |
| 2% Dimethyl Cocoamidopropyl Amine Oxide[3] | 9.2 |
| 5% Dimethyl Cocoamidopropyl Amine Oxide[3] | 9.7 |
| 10% Dimethyl Cocoamidopropyl Amine Oxide[3] | 9.0 |
| 2% N—Cocomorpholine-N—Oxide[4] | 21.5 |
| 5% N—Cocomorpholine-N—Oxide[4] | 12.6 |
| 10% N—Cocomorpholine-N—Oxide[4] | 10.9 |
| 2% Dimethyl N—alkyl ($C_{14}$, 50%; $C_{12}$, 40%; $C_{16}$, 10%) Amine Oxide[5] | *18.6 |
| 5% Dimethyl N—alkyl ($C_{14}$, 50%; $C_{12}$, 40%; $C_{16}$, 10%) Amine Oxide[5] | *20.4 |
| 10% Dimethyl N—alkyl ($C_{14}$, 50%; $C_{12}$, 40%; $C_{16}$, 10%) Amine Oxide[5] | *14.0 |
| Controls | |
| Water | *3.6 |
| 90% DMSO, 10% Water | 20.9 |

*Average of 2 or more determinations
[1] Barlox ® 10S
[2] Barlox ® 12
[3] Barlox ® C
[4] Barlox ® NCM
[5] Barlox ® 14

EXAMPLE 12

Tetracycline

TABLE IV
Percent Penetration Of 1% Tetracycline in 24 Hours

| Penetration Aid | |
|---|---|
| 2% Dimethyl Cocoamidopropyl Amine Oxide[1] | 38.4 |
| 5% Dimethyl Cocoamidopropyl Amine Oxide[1] | 53.9 |
| 10% Dimethyl Cocoamidopropyl Amine Oxide[1] | 32.9 |
| 2% Dimethyl Decyl Amine Oxide[2] | *8.4 |
| 5% Dimethyl Decyl Amine Oxide[2] | 14.5 |
| 10% Dimethyl Decyl Amine Oxide[2] | *12.8 |
| 2% Dimethyl N—Alkyl ($C_{12}$ - 69%, $C_{14}$ - 25%, $C_{16}$ - 6%) Amine Oxide[3] | 21.8 |
| 5% Dimethyl N—Alkyl ($C_{12}$ - 69%, $C_{14}$ - 25%, $C_{16}$ - 6%) Amine Oxide[3] | *67.6 |
| 10% Dimethyl N—Alkyl ($C_{12}$ - 69%, $C_{14}$ - 25%, $C_{16}$ - 6%) Amine Oxide[3] | *44.0 |
| 2% Dimethyl N—Alkyl ($C_{14}$ - 50%, $C_{12}$ - 40%, $C_{16}$ - 10%) Amine Oxide[4] | *6.8 |
| 5% Dimethyl N—Alkyl ($C_{14}$ - 50%, $C_{12}$ - 40%, $C_{16}$ - 10%) Amine Oxide[4] | *39.0 |
| 10% Dimethyl N—Alkyl ($C_{14}$ - 50%, $C_{12}$ - 40%, $C_{16}$ - 10%) Amine Oxide[4] | *38.1 |
| 2% Dimethyloctylamine oxide | *4.1 |
| 5% Dimethyloctylamine oxide | *5.1 |
| 10% Dimethyloctylamine oxide | *3.1 |
| 10% Dipropyl-6-hydroxyhexylamine oxide | 17.0 |
| 30% Dipropyl-6-hydroxyhexylamine oxide | 40.1 |
| 50% Dipropyl-6-hydroxyhexylamine oxide | 28.4 |
| 10% Tributylamine oxide | 6.0 |
| 30% Tributylamine oxide | 29.8 |
| 50% Tributylamine oxide | 31.6 |
| 70% Tributylamine oxide | 18.1 |
| 5% Diheptylmethylamine oxide | 8.6 |
| 10% Diheptylmethylamine oxide | 6.4 |
| 30% Diheptylmethylamine oxide | 4.5 |
| 10% N—Methyl Piperidine-N—Oxide | 9.6 |
| 2% N—Methyl Pyrrolidine-N—Oxide | 18.6 |
| 5% N—Methyl Pyrrolidine-N—Oxide | 55.4 |
| 10% N—Methyl Pyrrolidine-N—Oxide | 48.9 |
| Controls | |
| Ethanol/water (2/1) | 2.9 |

TABLE IV-continued

| Percent Penetration Of 1% Tetracycline in 24 Hours | |
|---|---|
| Water | *1.7 |

*Average of 2 or more determinations
[1]Barlox ® C
[2]Barlox ® 10S
[3]Barlox ® 12
[4]Barlox ® 14

EXAMPLE 13

5-FLUOROURACIL

TABLE V

| Percent Penetration of 1% 5-Fluorouracil in 24 Hours | |
|---|---|
| Penetration Aid | |
| 2% Dimethyl Decyl Amine Oxide | *46.0 |
| 2% Dimethyl N—alkyl ($C_{12}$ - 69%, $C_{14}$ - 25%, $C_{16}$ - 6%) Amine Oxide[1] | *56.9 |
| 5% Dimethyl N—alkyl ($C_{12}$ - 69%, $C_{14}$ - 25%, $C_{16}$ - 6%) Amine Oxide[1] | *52.2 |
| 10% Dimethyl N—alkyl ($C_{12}$ - 69%, $C_{14}$ - 25%, $C_{16}$ - 6%) Amine Oxide[1] | 78.9 |
| Control | |
| Water | *8.2 |

*Average of 2 or more determinations
[1]Barlox ® 12

EXAMPLE 14

Propanolol

TABLE VI

| Percent penetration of 1% - Propanolol in 24 Hours | |
|---|---|
| 2% dimethyl N—allyl($C_{12}$ - 69%, $C_{14}$ - 25%, $C_{16}$ - 6%) Amine Oxide[1] | *58.3 |
| 5% dimethyl N—allyl ($C_{12}$ - 69%, $C_{14}$ - 25%, $C_{16}$ - 6%) Amine Oxide[1] | *18.2 |
| Control | |
| Water | *3.5 |

[1]Barlox ® 12

EXAMPLE 15

Formulations

The following Table VI sets forth penetration data for various vehicles containing 1 percent hydrocortisone. The ingredients in the lotion and cream vehicles are provided hereinabove.

TABLE VII

| Percent Penetration of 1% Hydrocortisone From Various Vehicles in 24 Hours | |
|---|---|
| Vehicle | |
| 1% Hydroxyethylcellulose gel | 2.9 |
| 1% Hydroxyethylcellulose gel + 2% Dimethyl N—Alkyl ($C_{12}$ - 69%, $C_{14}$ - 50%, $C_{16}$ - 6%) Amine Oxide[1] | 23.2 |
| 1% Hyroxyethylcellulose gel + 5% Dimethyl N—Alkyl ($C_{12}$ - 69%, $C_{14}$ - 50%, $C_{16}$ - 6%) Amine Oxide | 24.6 |
| Lotion | 0.6 |
| Lotion + 5% Dimethyl N—Alkyl ($C_{14}$ - 50%, $C_{12}$ - 40% $C_{16}$ - 10%) Amine Oxide[2] | 29.2 |
| Cream | 1.9 |
| Cream + 5% Dimethyl N—Alkyl ($C_{14}$ - 50%, $C_{12}$ - 40%, $C_{16}$ - 10%) Amine Oxide | 13.4 |

What is claimed is:

1. A composition for topical application to animal skin comprising:
    (1) an effective amount of a therapeutic agent selected from the group consisting of erythromycin, benzoyl peroxide, hydrocortisone, tetracycline, 5-fluorouracil, and propranolol;
    (2) about 0.1 to 70 percent by weight of a water-soluble tertiary amine oxide; and
    (3) at least 1 molecule of water for every molecule of said amine oxide; said composition exhibiting at least 50 percent greater penetration of said therapeutic agent through mouse skin in 24 hours than a control composition without said amine oxide.

2. The composition according to claim 1 further comprising an extending medium compatible with the skin of the animal to which said composition is applied.

3. The composition according to claims 1 or 2 wherein said amine oxide is selected from the group consisting of:

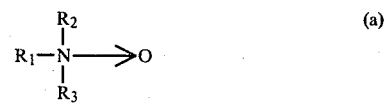

where $R_1$, $R_2$ and $R_3$ are saturated or unsaturated aliphatic radicals optionally containing, amide or ether linkages and pendent hydroxy groups and the total number of carbon atoms in $R_1+R_2+R_3$ does not exceed 28;

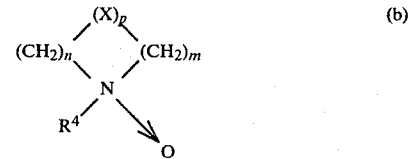

X is —O— or N-$R^5$, $R^4$ and $R^5$ are saturated or unsaturated aliphatic radicals each containing 1–18 carbon atoms optionally containing ether linkages or pendent hydroxyl groups;

P is zero or 1; n is 2 or 3 and m is 2, 3 or 4.

4. The composition according to claim 1 wherein said amine oxide is selected from the group consisting of trimethylamine oxide, tributylamine oxide, diheptylmethylamine oxide, dimethyldecylamine oxide, dimethyldodecylamine oxide, dimethylcocoamidopropylamine oxide, dipropyl-6-hydroxyhexylamine oxide, dicyclohexylmethylamine oxide, dimethyltetradecylamine oxide, and mixtures thereof.

5. The composition according to claim 1 wherein said amine oxide is selected from the group consisting of N-cocomorpholine-N-oxide, N-methylpyrrolidine-N-oxide, N-methylmorpholine-N-oxide, and N-methylpiperidine-N-oxide.

6. The composition according to claim 1 comprising 0.1 to 99 percent by weight of water.

7. The composition according to claim 1 comprising about 2 to 10 percent by weight of said amine oxide.

8. A method for the topical treatment or prevention of a disorder of the animal body comprising applying to the skin of said animal body an effective amount of the composition according to claim 1.

* * * * *